United States Patent
Kim et al.

(10) Patent No.: US 9,421,527 B2
(45) Date of Patent: Aug. 23, 2016

(54) INORGANIC NANOPARTICLE DEPOSITED CATALYST FOR HYDROGENATION AND MANUFACTURING METHOD OF THE SAME, AND HYDROGENATION FOR BIOMASS DERIVED HYDROCARBON COMPOUNDS

(71) Applicant: POSTECH ACADEMY-INDUSTRY FOUNDATION, Gyeongsangbuk-do (KR)

(72) Inventors: Dong-Pyo Kim, Gyeongsangbuk-do (KR); Ajay K. Singh, Gyeongsangbuk-do (KR)

(73) Assignee: Postech Academy-Industry Foundation, Gyeongsangbuk-do (KR)

( * ) Notice: Subject to any disclaimer, the term of this patent is extended or adjusted under 35 U.S.C. 154(b) by 0 days.

(21) Appl. No.: 14/513,529

(22) Filed: Oct. 14, 2014

(65) Prior Publication Data

US 2015/0224484 A1 Aug. 13, 2015

(30) Foreign Application Priority Data

Feb. 13, 2014 (KR) ........................ 10-2014-0016700

(51) Int. Cl.
*B01J 27/24* (2006.01)
*C07C 41/18* (2006.01)
(Continued)

(52) U.S. Cl.
CPC ...... *B01J 27/24* (2013.01); *B01J 21/18* (2013.01); *B01J 23/42* (2013.01); *B01J 23/44* (2013.01); *B01J 23/50* (2013.01); *B01J 23/52* (2013.01); *B01J 23/745* (2013.01); *B01J 23/75* (2013.01); *B01J 23/8906* (2013.01); *B01J 23/8913* (2013.01); *B01J 35/002* (2013.01);
(Continued)

(58) Field of Classification Search
CPC ............ B01J 27/44; B01J 21/00; B01J 21/18; B01J 21/185; B01J 23/44; B01J 23/48; B01J 23/50; B01J 23/52; B01J 23/75; B01J 23/745

See application file for complete search history.

(56) References Cited

FOREIGN PATENT DOCUMENTS

| JP | 2006-505400 A | 2/2006 |
| JP | 2011-195351 A | 6/2011 |

(Continued)

OTHER PUBLICATIONS

Liang, Y. et al. Nature Materials 2011, 10, pp. 780-786.*

(Continued)

*Primary Examiner* — Jafar Parsa
*Assistant Examiner* — Medhanit Bahta
(74) *Attorney, Agent, or Firm* — Riverside Law LLP

(57) ABSTRACT

A hydrogenation catalyst and a method of hydrogenating a hydrocarbon compound as a substrate using the same are provided. The hydrogenation catalyst includes inorganic nanoparticles and a nitrogen-doped reduced graphene oxide support for supporting the inorganic nanoparticles, and the hydrocarbon compound is derived from a biomass and contains a functional group. Therefore, the hydrogenation catalyst which exhibits a high conversion rate and high selectivity, is stable, and can be easily separated after a hydrogenation reaction, and whose catalytic activities are not significantly altered even when recovered and repeatedly recycled can be provided. The method of hydrogenating a hydrocarbon compound in which hydrogen can be directly produced in a reactor using formic acid as a hydrogen source without supplying additional hydrogen gas and simultaneously be used under normal pressure can also be provided.

18 Claims, 7 Drawing Sheets

(51) Int. Cl.

| | |
|---|---|
| C07C 29/17 | (2006.01) |
| C07C 45/62 | (2006.01) |
| C07C 51/36 | (2006.01) |
| C07D 311/60 | (2006.01) |
| C07C 5/03 | (2006.01) |
| C07C 209/36 | (2006.01) |
| C07C 221/00 | (2006.01) |
| B01J 23/44 | (2006.01) |
| B01J 23/745 | (2006.01) |
| B01J 23/89 | (2006.01) |
| B01J 23/75 | (2006.01) |
| C07C 37/00 | (2006.01) |
| C07C 41/01 | (2006.01) |
| C07C 231/10 | (2006.01) |
| B01J 37/03 | (2006.01) |
| B01J 37/16 | (2006.01) |
| B01J 37/34 | (2006.01) |
| B01J 21/18 | (2006.01) |
| B01J 23/42 | (2006.01) |
| B01J 23/50 | (2006.01) |
| B01J 23/52 | (2006.01) |
| B01J 35/00 | (2006.01) |
| C07C 1/22 | (2006.01) |
| C07C 5/08 | (2006.01) |

(52) U.S. Cl.
CPC ............ *B01J35/0013* (2013.01); *B01J 37/031* (2013.01); *B01J 37/16* (2013.01); *B01J 37/343* (2013.01); *C07C 1/22* (2013.01); *C07C 5/03* (2013.01); *C07C 5/08* (2013.01); *C07C 29/172* (2013.01); *C07C 37/002* (2013.01); *C07C 41/01* (2013.01); *C07C 41/18* (2013.01); *C07C 45/62* (2013.01); *C07C 51/36* (2013.01); *C07C 209/36* (2013.01); *C07C 221/00* (2013.01); *C07C 231/10* (2013.01); *C07D 311/60* (2013.01); *C07C 2101/14* (2013.01); *C07C 2103/18* (2013.01); *C07C 2521/18* (2013.01); *C07C 2523/89* (2013.01); *Y02P 20/52* (2015.11)

(56) References Cited

FOREIGN PATENT DOCUMENTS

| | | |
|---|---|---|
| KR | 10-2013-0012900 | 2/2013 |
| KR | 10-2013-0074904 | 7/2013 |
| KR | 10-2013-0079389 | 7/2013 |

OTHER PUBLICATIONS

Xu, et al. "Synthesis of Palladium Nanoparticles Supported on Mesoporous N-Doped Carbon and Their Catalytic Ability for Biofuel Upgrade," *J. Am. Chem. Soc.*, 2012, 134:16987-16990.

Kim, et al., "Chlorination of Reduced Graphene Oxide Enhances the Dielectric Constant of Reduced Graphene Oxide/Polymer Composites," *Adv. Mater.*, 2013, 25:2308-2313.

Singh, et al., Synthesis of metallic nanoparticle supported on N-doped graphene oxide and their catalytic ability to hydrogenation, *The 112th General Meeting of the Korean Chemical Society*.

He, et al., "Nitrogen-doped reduced graphene oxide supports for noble metal catalysts with greatly enhanced activity and stability," Applied Catalysis B: Environmental, 2013, vol. 132-133, pp. 379-388.

* cited by examiner

INORGANIC NANOPARTICLE DEPOSITED CATALYST FOR HYDROGENATION AND MANUFACTURING METHOD OF THE SAME, AND HYDROGENATION FOR BIOMASS DERIVED HYDROCARBON COMPOUNDS

CROSS-REFERENCE TO RELATED APPLICATION

This application claims priority to and the benefit of Korean Patent Application No. 2014-0016700, filed on Feb. 13, 2014, the disclosure of which is incorporated herein by reference in its entirety.

BACKGROUND

1. Field of the Invention

The present invention relates to a stable heterogeneous catalyst capable of being used for hydrogenation, a method of preparing the same, and a method of hydrogenating a biomass-derived hydrocarbon compound using the heterogeneous catalyst, which is able to produce high-value-added chemicals by defunctionalizing a biomass (desorption of a functional group).

2. Discussion of Related Art

With the exhaustion of fossil fuels, biomasses have attracted attention as alternative fuels. The use of catalysts having two metals supported therein is effective in converting a biomass into much valuable chemicals by defunctionalizing the biomass (desorption of a functional group). However, it is difficult to prepare such heterogeneous catalysts under the control at a molecular level.

Aromatic carbon-based graphene is known to be used as a support for heterogeneous catalysts. This is due to the electrical, optical, thermal, mechanical characteristics of graphene, and carbon nanostructures associated with graphene. Among various kinds of graphene, a graphene oxide (hereinafter abbreviated as 'GO') exhibiting good dispersibility has been widely used since it can be prepared using the simplest synthesis methods. GO can be used as a catalyst since it functions as a support for nano-materials due to many functional groups and a wide area. Up to now, GO has been used as a catalyst after being bound to metals, metal oxides, semiconductors, or magnetic nano-materials.

However, when the metals, metal oxides, semiconductors or magnetic nano-materials are supported in GO, it is impossible to ensure stability as a support.

Meanwhile, a hydrogen fuel is a clean fuel which produces no pollutants such as carbon dioxide while generating a great amount of energy upon combustion. However, since it is difficult to produce, store and transport the hydrogen fuel, it has not yet been able to replace the conventional fossil fuels. In recent years, hydrogen has been increasingly consumed, and 84% of the fossil fuels have been used after petroleum is purified by removing elements such as oxygen, nitrogen and sulfur. Also, a synthesis procedure such as preparation of drugs requires at least one hydrogenation operation. Although it is apparent that hydrogen is a valuable material, the use of hydrogen is limited due to difficulty in handling and high risk of explosion. Therefore, there is a demand for development of a method by which hydrogen can be directly produced in a reactor and simultaneously used for a hydrogenation reaction rather than a method of injecting hydrogen gas from the outside upon purification of petroleum and the hydrogenation reaction. In light of this, since one molecule of hydrogen and one molecule of carbon dioxide are produced by decomposition of formic acid, formic acid has attracted attention as a liquid source for producing hydrogen.

To decompose formic acid, homogeneous or heterogeneous catalysts are required. Among these, the homogeneous catalysts have a problem in that they are not easily separated from products after a reaction, and the heterogeneous catalysts have a problem in that their activities decreases with an increase in reaction time since metal nanoparticles are used as the heterogeneous catalysts. Also, the severe conditions for decomposition of formic acid promote detachment of a metal catalyst from a GO support.

As one example of the prior-art documents associated with these techniques, Korean Unexamined Patent Publication No. 10-2013-0074904 (published on Jul. 5, 2013) discloses catalysts which include a graphene oxide support and at least one functional group selected from the group consisting of carboxylic acid, sulfonic acid and phosphoric acid, the functional group being supported in the graphene oxide support, especially catalysts suitable for preparation of levulinic acid or ester compounds thereof derived from biomasses.

As another example of the prior-art documents, Korean Unexamined Patent Publication No. 10-2013-0079389 (published on Jul. 10, 2013) disclosed a method of preparing a biofuel which involves treating an organic matter with an aqueous solvent and one or more catalysts at a temperature of 250° C. to 400° C. and a pressure of 100 bar to 300 bar. Here, at least one catalyst selected from the group consisting of an alkali metal formate catalyst, a transition metal formate catalyst, a reactive carboxylic acid catalyst, a transition metal catalyst, a sulfide catalyst, a noble metal catalyst, a water-gas transfer catalyst, and a combination thereof may be used as the catalyst for promoting introduction of hydrogen, and at least one catalyst selected from the group consisting of an acid catalyst, a transition metal catalyst, a noble metal catalyst, a supported transfer metal catalyst, a solid acid catalyst, and a mixture thereof may be used as the catalyst for promoting removal of oxygen from an organic matter.

In addition, Korean Unexamined Patent Publication No. 10-2013-0012900 (published on Jan. 5, 2013) disclose a catalyst including inorganic nanoparticles coated with an organic ligand and a graphene oxide nanosheet for supporting the inorganic nanoparticles, wherein the catalyst exhibits high catalytic activities in a reduction of a nitroarene-based compound and has improved catalyst stability.

By way of example, the catalysts disclosed in the above-described prior-art documents show high selectivity and satisfactory conversion rates, but have problems in that the catalytic activities may be degraded upon recovery and repeated recycling after a hydrogenation reaction. Further, there is no report on the functions of catalysts applicable to two continuous procedures such as generation of hydrogen by decomposition of formic acid and application of hydrogen to a hydrogenation reaction.

Meanwhile, much research is being conducted recently on preparing biofuels. One typical example is defunctionalization of vanillin (desorption of a functional group). However, catalytic reactions reported in the prior art occur under the certain conditions (50 psi, 100° C. or 1 mPa, 90° C.: *Journal of the American Chemical Society* 134, 16987-16990, 2012) in which pressurization has to be realized by directly supplying hydrogen from the outside.

SUMMARY OF THE INVENTION

The present invention is directed to a hydrogenation catalyst which is stable and exhibits a high conversion rate and high selectivity for hydrogenation by removing functional groups from a biomass, preferably an aromatic compound containing a carbonyl group derived from the biomass.

Also, the present invention is directed to a hydrogenation catalyst whose catalytic activities are not significantly altered even when easily separated, recovered and repeatedly used after a hydrogenation reaction.

In addition, the present invention is directed to method of hydrogenating a biomass-derived hydrocarbon compound which may be performed under mild reaction conditions for hydrogenation by removing functional groups from a biomass, preferably an aromatic compound containing a carbonyl group derived from the biomass, and thus can minimize reaction procedures, reduce the risks caused by the supply of additional hydrogen gas, and separate and recycle the catalyst from products after a reaction.

Further, the present invention is directed to a method which involves ultimately preparing a high-value-added hydrocarbon compound from an inexpensive biomass, wherein the hydrocarbon compound may be easily prepared with high yield and high selectivity.

However, the technical objects of the present invention are not limited thereto, and other objects of the present invention which are not disclosed herein will become more apparent to those of ordinary skill in the art by describing in detail exemplary embodiments thereof.

According to an aspect of the present invention, there is provided a hydrogenation catalyst including inorganic nanoparticles and a nitrogen-doped reduced graphene oxide support for supporting the inorganic nanoparticles.

In the hydrogenation catalyst according to one exemplary embodiment, the inorganic nanoparticles may be selected from the group consisting of metal nanoparticles, a metal oxide, and a combination thereof.

In the hydrogenation catalyst according to another exemplary embodiment, the inorganic nanoparticles may be selected from the group consisting of palladium nanoparticles, gold nanoparticles, silver nanoparticles, cobalt nanoparticles, $Fe_3O_4$ nanoparticles, and a combination thereof.

In the hydrogenation catalyst according to still another exemplary embodiment, the inorganic nanoparticles may include silver nanoparticles, palladium nanoparticles, and $Fe_3O_4$ nanoparticles.

In the hydrogenation catalyst according to yet another exemplary embodiment, the inorganic nanoparticles may have an average particle size of 3 to 10 nm.

In the hydrogenation catalyst according to one exemplary embodiment, the catalyst may include the inorganic nanoparticles at a content of 1 to 5 atomic %.

According to another aspect of the present invention, there is provided a method of preparing a hydrogenation catalyst, which includes obtaining a nitrogen-doped reduced graphene oxide by reacting a nitrogen-containing compound with a colloidal suspension of graphene oxide; obtaining a dispersion of the nitrogen-doped reduced graphene oxide by dispersing the nitrogen-doped reduced graphene oxide in water; dispersing the dispersion of the nitrogen-doped reduced graphene oxide by adding an aqueous solution of an inorganic nanoparticle precursor to the dispersion of the nitrogen-doped reduced graphene oxide; and adding a reducing agent to perform a reaction.

In the method of preparing a hydrogenation catalyst according to one exemplary embodiment of the present invention, the inorganic nanoparticle precursor may be selected from the group consisting of a chloride, a sulfate, a nitrate, a carbonate of the inorganic nanoparticle, and a mixture thereof.

In the method of preparing a hydrogenation catalyst according to one exemplary embodiment of the present invention, the reducing agent that may be used herein may be selected from the group consisting of hydrazine, hydrazine hydrate, a borohydride, sodium borohydride, and a mixture thereof.

According to still another aspect of the present invention, there is provided a method of hydrogenating a biomass-derived hydrocarbon compound, which includes a hydrogenation operation of allowing a hydrocarbon compound as a substrate to react with a hydrocarbon catalyst in the presence of a hydrogen source, wherein the hydrocarbon compound is derived from a biomass and contains a functional group, and the hydrocarbon catalyst includes inorganic nanoparticles and a nitrogen-doped reduced graphene oxide support for supporting the inorganic nanoparticles.

In the method of hydrogenating a biomass-derived hydrocarbon compound according to one exemplary embodiment, the hydrogen source may be formic acid.

In the method of hydrogenating a biomass-derived hydrocarbon compound according to one exemplary embodiment of the present invention, the hydrogenation operation may be performed without supplying hydrogen gas from the outside of a reactor.

In the method of hydrogenating a biomass-derived hydrocarbon compound according to one exemplary embodiment of the present invention, the hydrogenation operation may be performed under reaction conditions of 80 to 130° C. and 6 to 12 hours.

In the method of hydrogenating a biomass-derived hydrocarbon compound according to one exemplary embodiment, the hydrogen source may be used at an equivalent content of 1.5 to 3.5 moles, based on the total content of the substrate.

In the method of hydrogenating a biomass-derived hydrocarbon compound according to one exemplary embodiment, the catalyst may be used at a content of 1.8 to 4.0 g per mole of a reaction product, based on the total content of the inorganic nanoparticles included in the hydrocarbon catalyst.

In the method of hydrogenating a biomass-derived hydrocarbon compound according to specific embodiments, the substrate may be at least one compound selected from the group consisting of an aromatic compound containing a carbonyl group, a hydrocarbon compound containing an alkene group, a hydrocarbon compound containing an alkyne group, and a hydrocarbon compound containing a nitro group. According to more specific embodiments, the substrate may be vanillin.

In the method of hydrogenating a biomass-derived hydrocarbon compound according to the present invention, the catalyst may satisfy the above-described requirements such as the kinds of the inorganic nanoparticles, the size of the nanoparticle, a mixing ratio of the inorganic nanoparticle and the graphene oxide.

The method of hydrogenating a biomass-derived hydrocarbon compound according to one exemplary embodiment may further include recovering the hydrocarbon catalyst after the hydrogenation operation, and the recovering of the hydrocarbon catalyst may be performed using at least one method selected from the group consisting of centrifugation, filtration, and a magnetic method.

BRIEF DESCRIPTION OF THE DRAWINGS

The above and other objects, features and advantages of the present invention will become more apparent to those of ordinary skill in the art by describing in detail exemplary embodiments thereof with reference to the accompanying drawings, in which.

DETAILED DESCRIPTION OF EXEMPLARY EMBODIMENTS

Figure 1:
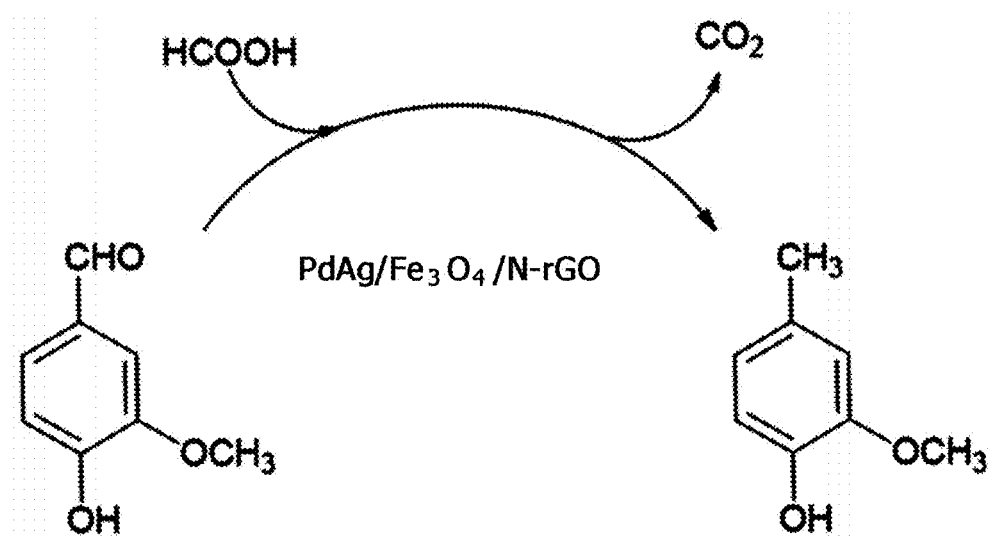
FIG. 1 is a formula showing a hydrogenation method in which decomposition of formic acid into hydrogen and hydrogenation of an organic compound are performed according to one exemplary embodiment of the present invention.

Exemplary embodiments of the present invention will be described in detail below with reference to the accompanying drawings. While the present invention is shown and described in connection with exemplary embodiments thereof, it will be apparent to those skilled in the art that various modifications can be made without departing from the scope of the invention.

Unless specifically stated otherwise, all the technical and scientific terms used in this specification have the same meanings as what are generally understood by a person skilled in the related art to which the present invention belongs. In general, the nomenclatures used in this specification and the experimental methods described below are widely known and generally used in the related art.

An object of the present invention is to convert a hydrocarbon compound into more valuable chemicals by substitution of various functional groups such as an alkyne group, an alkene group, an aldehyde group, a ketone group, and a nitro group in the hydrocarbon compound. The present invention provides a new catalyst in which metal nanoparticles having double functions are fixed in a graphene substrate. Here, the catalyst is a hydrogenation catalyst including inorganic nanoparticles and a nitrogen-doped reduced graphene oxide support for supporting the inorganic nanoparticles.

In such a catalyst, the inorganic nanoparticles are not particularly limited. For example, the inorganic nanoparticles may be selected from the group consisting of metal nanoparticles, a metal oxide, and a combination thereof. Considering the activities of the catalyst, the inorganic nanoparticles may preferably be selected from the group consisting of palladium nanoparticles, gold nanoparticles, silver nanoparticles, cobalt nanoparticles, Fe$_3$O$_4$ nanoparticles, and a combination thereof. Here, when the inorganic nanoparticles essentially include the palladium nanoparticles, selectivity may be improved. In addition, when the inorganic nanoparticles include the Fe$_3$O$_4$ nanoparticles, dispersibility in an aqueous solution may be improved, a conversion rate may be enhanced, and the catalyst may be more easily separated and recovered. Further, when the inorganic nanoparticles include the Ag nanoparticles, the inorganic nanoparticles may function as a catalytic activity promoter to achieve the highest selectivity and conversion rate. In consideration of these facts, the most preferred catalyst may include silver nanoparticles, palladium nanoparticles and Fe$_3$O$_4$ nanoparticles as the inorganic nanoparticles.

In the catalyst according to one exemplary embodiment of the present invention, the support for supporting such inorganic nanoparticles is a nitrogen-doped reduced graphene oxide. The nitrogen-doped reduced graphene oxide is obtained by allowing a graphene oxide to react with a compound containing a nitrogen atom so that the nitrogen atom can be included in the graphene structure in addition to oxygen atoms. The nitrogen and oxygen atoms in the graphene structure may bind to a metal. As a result, metal nanoparticles may be polydispersed, thereby preventing a re-oxidation reaction and condensation of the metal. Therefore, the catalyst has advantages in that stability of the catalyst may be enhanced, and the original catalytic activity may be maintained even when repeatedly recycled. In a process of hydrogenating a hydrocarbon compound by generating hydrogen during a reaction using formic acid as a hydrogen source as will be described later, it is also possible to prevent the metal nanoparticles from being detached from the support.

In the catalyst according to one exemplary embodiment of the present invention, a nitrogen-doped reduced graphene oxide that is the support may be more desirable as the content of nitrogen used to dope a graphene oxide increases. However, the content of the nitrogen atoms included in the nitrogen-doped reduced graphene oxide may be approximately 4 atomic % in consideration of a reaction used for preparation of the nitrogen-doped reduced graphene oxide.

In the detailed description set forth above or later, the term 'atomic %' refers to a value obtained by analysis of elements in a sample using XPS analysis. Here, the value may be defined as a percentage of atomic weights of the elements forming the sample.

The inorganic nanoparticles supported in the nitrogen-doped reduced graphene oxide used as the support may be present in a state in which the inorganic nanoparticles are uniformly monodispersed in the catalyst. In this case, the dispersed nanoparticles may have an average particle size of approximately 3 to 10 nm, preferably approximately 5 to 7 nm. Within this average particle size range, the catalyst having the inorganic nanoparticles monodispersed therein may have improved catalytic stability and catalytic activity.

In the catalyst according to one exemplary embodiment, dispersibility of the inorganic nanoparticles into the support, and selectivity and a conversion rate upon application of the catalyst may be improved when the catalyst includes the inorganic nanoparticles at a content of approximately 1 to 5 atomic %.

According to another exemplary embodiment of the present invention, there is provided a method for preparing a hydrogenation catalyst. Here, the method may include allowing a nitrogen-containing compound to react with a colloidal suspension of a graphene oxide to obtain a nitrogen-doped reduced graphene oxide, peeling and dispersing the nitrogen-doped reduced graphene oxide using a dispersion system such as ultrasonic waves, and reacting with an aqueous solution of an inorganic nanoparticle precursor to obtain a hydrogenation catalyst.

A method of preparing a graphene oxide (GO) is not particularly limited. For example, the graphene oxide (GO) may be prepared by oxidizing graphite powder using a Hummer method (see Kim, J. Y. et al. Chlorination of Reduced Graphene Oxide Enhances the Dielectric Constant of Reduced Graphene Oxide/Polymer Composites. *Advanced Materials* 25, 2308-2313, doi:10.1002/adma.201300385 (2013)).

The graphite powder obtained thus may be dispersed in water, and treated with ultrasonic waves to prepare a suspension. Thereafter, a nitrogen-containing compound, particularly, hydrazine monohydrate, may be added to the suspension, and heated at 80 to 130° C. for 6 to 12 hours to obtain a nitrogen-doped reduced graphene oxide.

The resulting nitrogen-doped reduced graphene oxide may be dissolved in water, and then exposed to ultrasonic waves to obtain a uniform dispersion.

When an aqueous solution of an inorganic nanoparticle precursor is added to such a suspension of a nitrogen-doped reduced graphene oxide to react therewith, and a reducing agent is added to the resulting reaction mixture, the hydrogenation catalyst of the present invention including a nitrogen-doped reduced graphene oxide support and inorganic nanoparticles may be finally obtained.

In this case, at least one selected from the group consisting of a chloride, a sulfate, a nitrate and a carbonate of the inorganic nanoparticles, and a mixture thereof may be used as the inorganic nanoparticle precursor.

At least one selected from the group consisting of hydrazine, hydrazine hydrate, a borohydride, sodium borohydride and a mixture thereof may be used as the reducing agent.

The above-described method is not limited to a method of loading the inorganic nanoparticles onto the nitrogen-doped reduced graphene oxide.

According to still another exemplary embodiment of the present invention, there is provided a method of hydrogenating a biomass-derived hydrocarbon compound, which includes a hydrogenation operation of allowing a hydrocarbon compound as a substrate to react with the above-described catalyst according to exemplary embodiments in the presence of a hydrogen source. Here, the hydrocarbon compound is derived from a biomass and contains a functional group.

Biomass is the term used in the field of ecology, and refers to a mass of any living organism such as an animal, a plant or a microorganism. Therefore, representative biomasses include stems, roots and leaves of woods, and dead organic matters, that is, organic waste matters (waste resources, animal dung, etc.), are excluded from the ecological meaning of biomasses. However, with the acceleration of global warming and introduction of the concept of 'sustainable development,' the meaning of the term "biomass" has extended to refer to "biogenic materials include foods, fuels, materials, and resources" since 1970.

Biomasses may be mainly divided into a production system and a wasting system. For example, the production-system biomass may include forage crops, and fuel crops, for example, glycan (i.e., sugar cane), starch, lignocelluloses, and the like, and the wasting-system biomass may include an agricultural biomass such as rice straw and rice husks, a livestock biomass such as animal dung, a forest biomass such as sawdust, food wastes, grass, sludge, and the like.

To provide a method useful in preparing a high-value-added compound such as a biomass, the present invention provides use of the catalyst according to the present invention as described above.

According to one specific embodiment, there is a provided a method capable of obtaining a high-value-added compound by hydrogenating a biomass, preferably various hydrocarbon compounds derived from the biomass, and, more particularly, a hydrocarbon-based compound containing a functional group.

A substrate applicable to the hydrogenation method may be a hydrocarbon-based compound which is derived from the biomass and contains various functional groups. According to one specific embodiment, at least one compound selected from the group consisting of an aromatic compound containing a carbonyl group, a hydrocarbon compound containing an alkene group, a hydrocarbon compound containing an alkyne group, and a hydrocarbon compound containing a nitro group may be used as the substrate. According to one more specific embodiment, the substrate may be vanillin.

Over the past few decades, many attempts have been conducted to commercialize lignin. Lignin is a material which has a complicated structure in which various molecular sieves are entangled, and can decompose into various compounds like petroleum. Vanillin is a pyrolytic oil extracted from lignin, and thus may be used as a biofuel through a hydrogenation reaction.

When the substrate is generally prepared into compounds reduced through a hydrogenation reaction, a hydrogenation catalyst and a hydrogen source are required. In general, a separately supplied hydrogen gas may be used as the hydrogen source. However, this is not desirable in consideration of the risks of the hydrogen gas.

Therefore, in the present invention, hydrogen is produced during a hydrogenation reaction, and a hydrogenation reaction is performed using such produced hydrogen. For this purpose, formic acid may be used as the hydrogen source in the hydrogenation method according to the present invention.

Formic acid is a material that can produce one molecule of hydrogen and one molecule of carbon dioxide when decomposed.

In this way, hydrogen produced by decomposition of formic acid may be used for hydrogenation of a biomass, particularly hydrogenation of vanillin, without injecting additional hydrogen gas.

For this purpose, decomposition of formic acid into hydrogen and hydrogenation of a substrate in a reactor should be performed at the same time. This may be achieved using the above-described hydrogenation catalyst according to the present invention. That is, when a graphene catalyst in which the above-described inorganic nanoparticles according to the present invention are fixed participates in a chemical reaction, the graphene catalyst may be used after decomposing formic acid into hydrogen and carbon dioxide and applying the adsorbed hydrogen to a hydrogenation reaction or a hydrodeoxygenation reaction.

When the hydrogenation catalyst according to the present invention is used, a single reaction in which hydrogen is produced from formic acid under a general condition of normal pressure and directly used for defunctionalization (desorption of a functional group) may be realized, unlike a conventional method in which synthesis and application of hydrogen, that is, a two-step reaction, generally occur under pressurized and special conditions. That is, decomposition of formic acid into hydrogen and hydrogenation or hydrodeoxygenation of various organic compounds may be continuously carried out in an aqueous solution under normal pressure conditions. These reactions may be represented by a formula, as shown in FIG. 1.

A mechanism in which the decomposition of formic acid into hydrogen and the hydrogenation of a substrate are continuously carried out using the hydrogenation catalyst according to the present invention is not particularly limited. For example, dissociative adsorption of a hydrogen source by metals in the catalyst is initiated, resulting in formation of a metal hydride complex with carbon dioxide produced during the decomposition of formic acid into hydrogen. Such a metal hydride complex is considered to reduce various functional groups.

Accordingly, the hydrogenation operation may be performed under reaction conditions of 80 to 130° C. and 6 to 12 hours.

By way of example, when a reaction is performed using vanillin as the substrate together with formic acid, an alternative fuel upgrading reaction in which a heat generation rate increases occurs upon oxidation caused by hydrogenation of vanillin. Vanillin is a bio-oil containing an aldehyde group, that is, a compound which itself has low energy density. However, when vanillin is subjected to a hydrogenation reaction in which the aldehyde group is substituted with a methyl group, vanillin may be used as an alternative fuel due to an increase in energy density.

In such a hydrogenation method according to one exemplary embodiment of the present invention, the hydrogen source, particularly, formic acid, may be used at an equivalent content of 1.5 to 3.5 moles, based on the total content of the substrate.

Also, the catalyst may be used at a content of 1.8 g to 4.0 g per mole of a reaction product, based on the total content of the inorganic nanoparticles included in the catalyst. The use of the catalyst in this content range may be desirable in an aspect of catalytic activities.

One advantage of the present invention may be that the catalyst may be easily recovered and recycled after such a hydrogenation reaction.

Accordingly, the hydrogenation method according to one exemplary embodiment of the present invention may include recovering the catalyst after the above-described hydrogenation operation, and the recovery of the catalyst may be simply performed using at least one method selected from the group consisting of centrifugation, filtration, and a magnetic method.

Even when the catalyst recovered in such a simple method is repeatedly used again in the hydrogenation reaction, there is little loss in activities. In experiments according to exemplary embodiments that will be described later, it could be seen that there was little loss in activities and selectivity was also maintained at a constant level even when the catalyst was repeatedly recycled 6 times. Then, element analysis of the recycled catalyst is performed. As a result, it could also be seen that there was little change in atomic content of the recycled catalyst.

Therefore, the hydrogenation catalyst according to the present invention exhibits significantly improved industrial applicability since the hydrogenation catalyst satisfies requirements such as high stability and easy separability and may be instantly recovered without any loss of activities.

Hereinafter, preferred exemplary embodiments of the present invention will be described in order to aid in understanding the present invention. However, it should be understood that the description set forth herein is merely exemplary and illustrative of exemplary embodiments for the purpose of describing the present invention, and is not intended to limit the exemplary embodiments.

EXAMPLE

S1. Material and Method Used in Experiments (1) Experimental Material
Graphite powder, sulphuric acid (95-97%), hydrogen peroxide (30 wt %), potassium permanganate, hydrazine hydrate (65% in water, Aldrich), formic acid (>99%), $Pd(NO_3)_2$, $AgNO_3$, $HAuCl_4$, $CoCl_2 \cdot 6H_2O$, $PtCl_2$, $FeCl_3$, $FeCl_2$ and all kinds of organic solvents were received from Sigma-Aldrich Chemicals.

In each experiment, deionized water (a conductivity of 18.2 mS) was used.

(2) Measurement Method
Wide angle X-ray diffractograms of the synthetic sample was performed using a Rigaku D/max 2500/PC X-ray diffractometer (Cu Ka (1.54056) radiation)

The surface morphology of thoroughly dried sample was analyzed by a TEM (JEOL JEM 2100F transmission electron microscope, W, Acc.v.: approximately 120 kV). The TEM samples were prepared by dispersing dry powder of catalyst in an ethanol solvent.

For scanning electron microscopy (SEM), gold sputter coating were carried out on desired samples at pressure ranging in between 1 and 0.1 Pa. Sample was loaded in the machine, and measured using Philip XL30 SEM ($10^{-2}$ to $10^{-3}$ Pa, EHT 15.00 kV, and 300 V collector bias).

All the XPS analyses were performed using SIGMA PROBE (ThermoVG, monochromic Al—Ka X-ray source (100 W)).

Centrifugation was performed using Gyrogen 1236 MG, and ultrasonication was performed using Power Sonic 405.

S2. Synthesis (1) Synthesis of Graphene Oxide (GO)
GO was prepared by the oxidation of graphite powder with reference to a Hummer method (see Kim, J. Y. et al. Chlorination of Reduced Graphene Oxide Enhances the Dielectric Constant of Reduced Graphene Oxide/Polymer Composites. *Advanced Materials* 25, 2308-2313, doi:10.1002/adma.201300385 (2013)).

In general, 10 g of graphite powder was added into 500 ml of concentrated $H_2SO_4$, and stirred on ice bath for an hour and then 40 g of $KMnO_4$ was slowly added thereto. The resulting reaction mixture was further stirred for 2 hours then ice bath was removed, and continuously stirred for 24 hours. The resulting reaction product was put on the ice bath, and 500 ml of deionized water was slowly added to dilute the reaction product. Thereafter, a hydrogen peroxide solution (30%) was added dropwise until the solution turned reddish brown. The resulting reddish brown solution was centrifuged at 800 rpm (for 10 minutes) to isolate an unexploited graphite oxide. Subsequently, the suspension was transferred to another centrifuge tube, and centrifuged at 4,000 rpm for 30 minutes to obtain a reddish brown solid material. The obtained solid material was washed thoroughly by repeated centrifugation with deionized water (until a pH value of the solution reached pH 6.6). The finally obtained solid material was dried under a reduced pressure to obtain a desired graphene oxide (GO).

(2) Synthesis of Nitrogen-Doped Reduced Graphene Oxide (N-rGO)

2 g of the GO powder synthesized in Operation (1) was dispersed in 1,000 ml of deionized water in a beaker, and sonicated for 3 hours to prepare a stable colloidal suspension. 15 ml of hydrazine monohydrate (65% in water) was put into the beaker, and continuously heated at 90° C. for 12 hours while stirring to obtain a powder of nitrogen-doped reduced graphene oxide (hereinafter referred to as N-rGO) that was a black precipitate. The powder was cooled to room temperature, and the solution was then centrifuged at 4,000 rpm for 10 minutes to collect the precipitate. The obtained black material was washed with deionized water, centrifuged, and dried under a high pressure to obtain a desired N-rGO powder.

(3) Synthesis of Magnetic Substance ($Fe_3O_4$)

A magnetic substance was synthesized with reference to a reported oxidation method (Kim, J. Y. et al. Chlorination of Reduced Graphene Oxide Enhances the Dielectric Constant of Reduced Graphene Oxide/Polymer Composites. *Advanced Materials* 25, 2308-2313, doi:10.1002/adma.201300385 (2013)).

An aqueous solution of $FeCl_3$ and $FeCl_2$ were mixed ($FeCl_3$=0.810 g/100 ml and $FeCl_2$=0.316 g/100 ml), and stirred for an hour. An ammonia solution was added dropwise to the resulting mixture so that a pH value of the solution was adjusted to pH 10. Thereafter, the temperature of solution was raised to 80° C., and stirred for an hour. The resulting black solution was filtered, washed with water and acetone several times, and finally dried at 70° C. under a vacuum.

(4) Synthesis of Palladium-Loaded Graphene (Pd/N-rGO)

2 g of the nitrogen-doped reduced graphene oxide synthesized thus was dissolved in 1 L of water, and then exposed to ultrasonic waves for 3 hours during ultrasonic cleaning to prepare a uniform dispersion (1). 0.5 mmol of $PdNO_3.2H_2O$ was dissolved in 25 ml of water, and then added to the dispersion (1) to prepare a solution (2). For uniform dispersion, the solution (2) was stirred for 2 hours to prepare a solution (3). 15 ml of an aqueous hydrazine solution (hydrazine monohydrate 65% in water) was added to the solution (3), and then stirred at 90° C. for 12 hours to synthesize a palladium-loaded graphene oxide (Pd/N-rGO). To collect the particles synthesized in the solution, the solution was centrifuged at 4,000 rpm for 10 minutes in a centrifuge to obtain a pellet of particles, and the supernatant was discarded. For a washing process, the pellet of particles was added to water, repeatedly centrifuged three times, and then dried at 70° C. in a drying oven.

(5) Synthesis of Magnetic Particle-Loaded Graphene ($Fe_3O_4$/N-rGO)

2 g of the nitrogen-doped reduced graphene oxide synthesized thus was dissolved in 1 L of water, and then exposed to ultrasonic waves for 3 hours during ultrasonic cleaning to prepare a uniform dispersion (1). An aqueous $FeCl_3$ solution (0.810 g in 25 ml of water) and an aqueous $FeCl_2$ solution (0.316 g in 25 ml of water) were slowly added to the dispersion (1) to prepare a solution (2). For uniform dispersion, the solution (2) was stirred for 2 hours to prepare a solution (3). An aqueous ammonia solution was added to the solution (3) until a pH value of the solution reached pH 10, thereby preparing a solution (4). 5 ml of an aqueous hydrazine solution (65% hydrazine monohydrate in water) was added to the solution (4), and then stirred at 90° C. for 12 hours to synthesize a magnetic particle-loaded graphene oxide. To collect the particles synthesized in the solution, the solution was centrifuged at 4,000 rpm for 10 minutes in a centrifuge to obtain a pellet of particles, and the supernatant was discarded. For a washing process, the pellet of particles was added to water, repeatedly centrifuged three times, and then dried at 70° C. in a drying oven.

(6) Synthesis of Metal-Loaded Magnetic Graphene Oxide (A/$Fe_3O_4$/N-rGO, wherein A=Co, Ag, Pd, Au, or Pt)

2 g of the nitrogen-doped reduced graphene oxide synthesized thus was dissolved in 1 L of water, and then exposed to ultrasonic waves for 3 hours during ultrasonic cleaning to prepare a uniform dispersion (1). An aqueous $FeCl_3$ solution (0.810 g in 25 ml of water) and an aqueous $FeCl_2$ solution (0.316 g in 25 ml of water) were slowly added to the dispersion (1) to prepare a solution (2). For uniform dispersion, the solution (2) was stirred for 2 hours to prepare a solution (3). To load a metal, each of $Pd(NO_3)_2$, $AgNO_3$, $HAuCl_4$, $CoCl_2.6H_2O$ and $PtCl_2$ aqueous solutions (0.5 mmol in 25 ml of water) was slowly added to the solution (3) to prepare a solution (4). For uniform dispersion, the solution (4) was stirred for 2 hours to prepare a solution (5). An aqueous ammonia solution was added to the solution (5) until a pH value of the solution reached pH 10, thereby preparing a solution (6). 5 ml of an aqueous hydrazine solution (65% hydrazine monohydrate in water) was added to the solution (6), and then stirred at 90° C. for 12 hours to synthesize a magnetic graphene oxide loaded with each metal. To collect the particles synthesized in the solutions, the solutions were centrifuged at 4,000 rpm for 10 minutes in a centrifuge to obtain a pellet of particles, and the supernatant was discarded. For a washing process, the pellet of particles was added to water, repeatedly centrifuged three times, and then dried at 70° C. in a drying oven.

(7) Synthesis of Magnetic Graphene Oxide Loaded With Two Metals (B/Pd/$Fe_3O_4$/N-rGO, Wherein B=Co, Ag, Au, or Pt)

2 g of the nitrogen-doped reduced graphene oxide synthesized thus was dissolved in 1 L of water, and then exposed to ultrasonic waves for 3 hours during ultrasonic cleaning to prepare a uniform dispersion (1). An aqueous $FeCl_3$ solution (0.810 g in 25 ml of water) and an aqueous $FeCl_2$ solution (0.316 g in 25 ml of water) were slowly added to the dispersion (1) to prepare a solution (2). For uniform dispersion, the solution (2) was stirred for 2 hours to prepare a solution (3). To load a metal, each of aqueous $AgNO_3$, $HAuCl_4$, $CoCl_2.6H_2O$ and $PtCl_2$ solutions (0.5 mmol in 25 ml of water) was slowly added to the solution (3) to prepare a solution (4). For uniform dispersion, the solution (4) was stirred for 10 minutes to prepare a solution (5). Thereafter, an aqueous $Pd(NO_3)_2$ solution (0.5 mmol in 25 ml of water) was added to the solution (5), and then stirred for 2 hours to prepare a solution (6). An aqueous ammonia solution was added to the solution (6) until a pH value of the solution reached pH 10, thereby preparing a solution (7). 5 ml of an aqueous hydrazine solution (65% hydrazine monohydrate in water) was added to the solution (7), and then stirred at 90° C. for 12 hours to synthesize a magnetic particle-loaded graphene oxide. To collect the particles synthesized in the solution, the solution was centrifuged at 4,000 rpm for 10 minutes in a centrifuge to obtain a pellet of particles, and the supernatant was discarded. For a washing process, the pellet of particles was added again to water, repeatedly centrifuged three times, and then dried at 70° C. in a drying oven.

S3. Hydrogenation Procedure of Vanillin

A procedure used to reduce vanillin is as follows:

A reactant (2.0 mmol, 304 mg), a catalyst (20 mg), $H_2O$ (2 mL), formic acid (2.5 equivalents), and anisole (1.0 mmol) were filled in a decompression tube (4 mL) sealed with a Teflon lid. The reaction mixture was heated at 80° C. or 130° C. for 10 hours in an oil bath, and then cooled to room temperature. The reaction mixture was extracted by adding 10 mL $CH_2Cl_2$ and centrifuged for 10 minutes to separate a catalyst. The resulting organic layer was analyzed using gas chromatography-mass spectrophotometry (GC-MS).

To perform hydrogenation of vanillin using the above-described process, a comparative experiment was performed using various combinations of catalysts. Specific kinds of catalysts, temperature conditions in hydrogenation reaction operations, and selectivities and conversion rates of the catalysts are summarized and listed in the following Table 1.

TABLE 1

| Entry | Catalyst | Temperature | BET area (m²/g) | Selectivity | TOF (h⁻¹) |
|---|---|---|---|---|---|
| 1 | GO | 130 | 558 | N/A | N/A |
| 2 | N-rGO | 130 | 230 | N/A | N/A |
| 3 | Fe₃O₄ | 130 | — | N/A | N/A |
| 4 | Fe₃O₄/N-rGO | 130 | 220 | N/A | N/A |
| 5 | Pd/N-rGO | 130 | 202 | 99 | 5 |
| 6 | Pd/Fe₃O₄/N-rGO | 130 | 202 | 99 | 19 |
| 7 | Ag/Fe₃O₄/N-rGO | 130 | 214 | N/A | N/A |
| 8 | Au/Fe₃O₄/N-rGO | 130 | 222 | N/A | N/A |
| 9 | Pt/Fe₃O₄/N-rGO | 130 | 226 | N/A | N/A |
| 10 | Co/Fe₃O₄/N-rGO | 130 | 210 | N/A | N/A |
| 11 | PdCo/Fe₃O₄/N-rGO | 130 | 152 | 92 | 29 |
| 12 | PdAu/Fe₃O₄/N-rGO | 130 | 260 | 99 | 9 |
| 13 | PdPt/Fe₃O₄/N-rGO | 130 | 201 | N/A | N/A |
| 14 | PdAg/Fe₃O₄/N-rGO | 130 | 252 | 99 | 302 |
| 15 | PdAg/Fe₃O₄/N-rGO | 80 | 252 | 99 | 3 |
| 16 | PdCoAu/Fe₃O₄/N-rGO | 130 | 206 | 96 | 37 |
| 17 | PdAg/N-rGO | 130 | 222 | 99 | 58 |
| 18[a] | Pd/C | 130 | 899[b] | 82 | 1 |

(Note)
N/A: No activity, and
TOF: Turnover frequency, which represent a conversion efficiency.

As seen from the results listed in Table 1, it could be seen that no reaction took place when the reaction was performed at 130° C. for 10 hours using GO, N-rGO, or the magnetic particles as the catalyst (Entries 1-3). After the magnetic particles were loaded onto N-rGO, the reaction was performed in the same manner as described above. The magnetic particles aid in improving dispersibility of N-rGO in an aqueous solution, may be mixed on a stirrer without using an additional stirrer bar, and function to promote separation of the catalyst from the aqueous solution using a magnet after the reaction. However, the reaction did not take place even when the catalyst was used (Entry 4).

Also, Pd was loaded onto N-rGO, and the same reaction was performed. As a result, the reaction proceeded with 99% selectivity (Entry 5). When both of Pd and the magnetic particles were loaded onto N-rGO, the catalyst exhibited 99% selectivity, and dispersibility was higher and TOF was 4 times in the presence of the magnetic particles, compared with Entry 5.

From these results, it could be seen that the use of the catalyst was more desirable when two or more inorganic nanoparticles were supported in the catalyst, compared with when the inorganic nanoparticles were supported alone (Entries 7 to 17). Among these, it was revealed that the PdAg/Fe₃O₄/N-rGO catalyst exhibited the highest selectivity and TOF value, and was best used for hydrogenation of vanillin (Entry 14).

However, it was revealed that the Au—Pd and Ag—Pd combinations apparently exhibited 99% selectivity, but TOF was much higher in the Ag—Pd combination than in the Au—Pd combination.

In addition, the three catalysts (Entries 16 to 18) were not advantageous, compared with the two metal catalysts, Ag and Pd.

Figure 2:
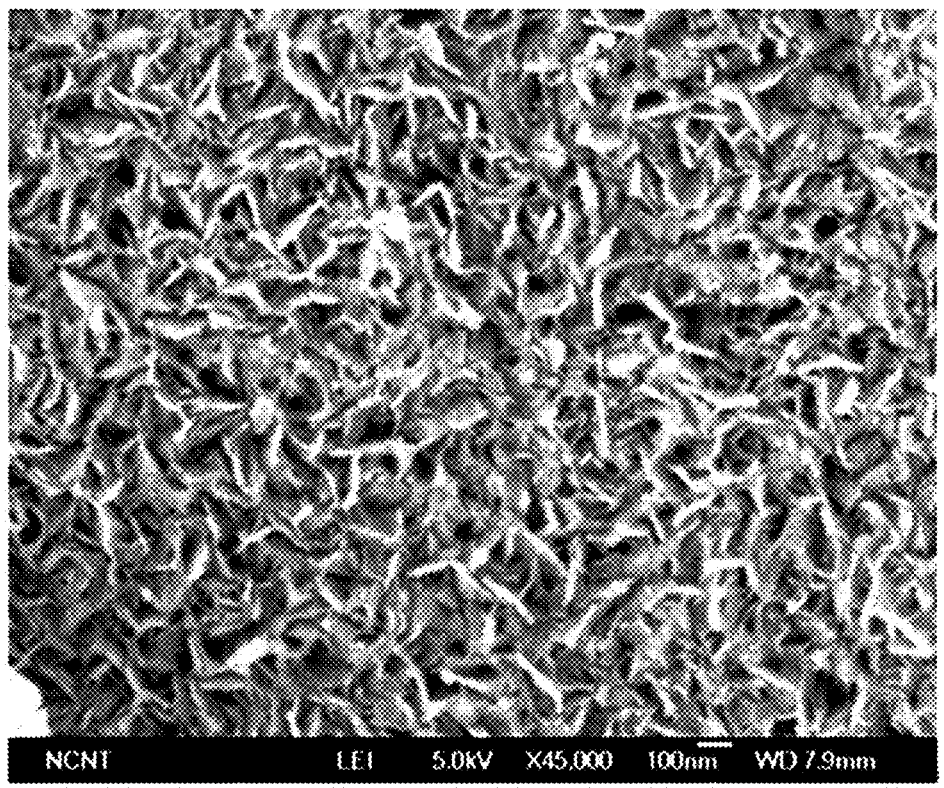
FIG. 2 is a scanning electron microscope (SEM) image of PdAg/Fe$_3$O$_4$/N-rGO.
Figure 3:
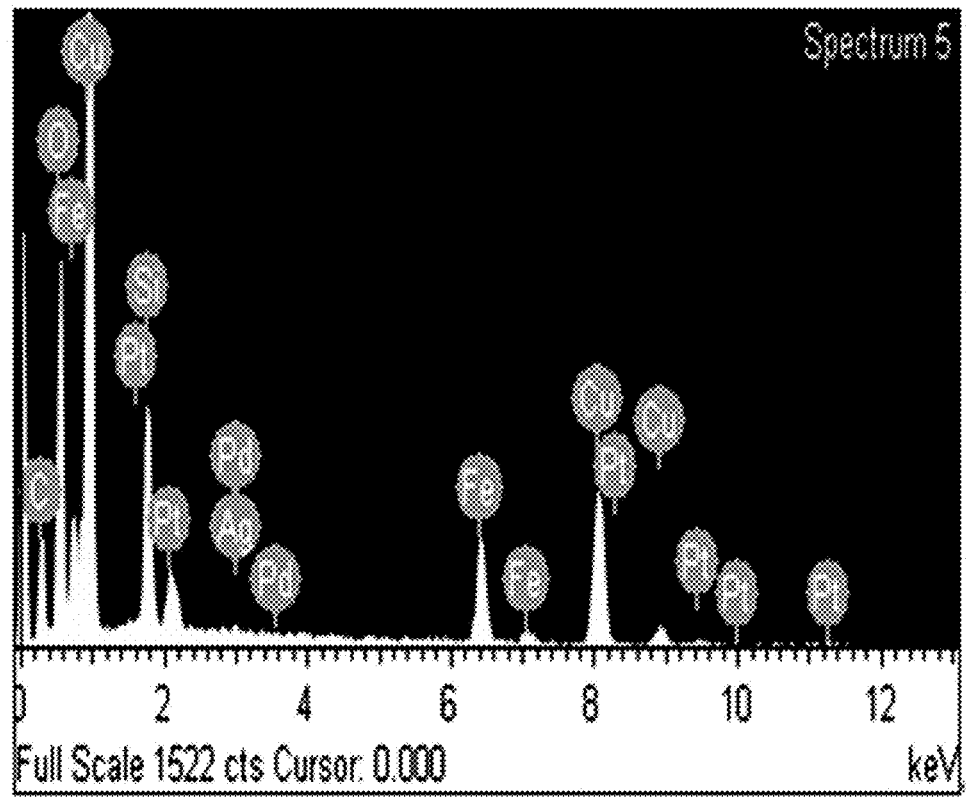
FIG. 3 shows the energy-dispersive X-ray (EDX) data of PdAg/Fe$_3$O$_4$/N-rGO.

Meanwhile, to determine the structures and innate characteristics of the respective catalysts listed in Table 1, various experiments were performed according to the above-described measurement methods. Among these catalysts, images of the PdAg/Fe₃O₄/N-rGO catalyst observed under SEM using EDX are shown in FIGS. 2 and 3. As shown in FIGS. 2 and 3, it could be seen that the catalyst was observed in the form of nanosheets similar to tiny rose petals. The element mapping results obtained through EDX analysis showed that the metals were uniformly dispersed on the catalyst.

Figure 4:
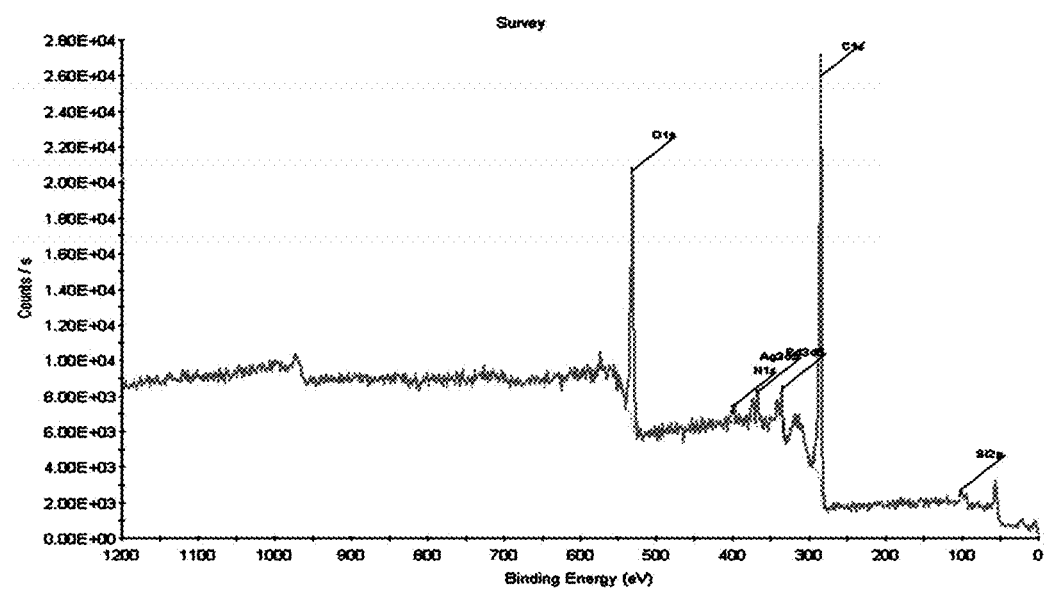
FIG. 4 shows X-ray photoelectron spectroscopy (XPS) signals of PdAg/Fe$_3$O$_4$/N-rGO.

Also, the catalysts were subjected to XPS analyses to determine the atomic percentages and binding characteristics of the constituent elements, and oxidation levels of the metals. Among these catalysts, the XPS analysis profile of PdAg/Fe₃O₄/N-rGO is shown in FIG. 4. From these results, it could be seen that the specific binding energy values of C, O and N in the PdAg/Fe₃O₄/N-rGO catalyst were determined The absence of satellite peaks observed at 7.19 eV in Fe peaks was considered to be associated with the main characteristics of $Fe^{3+}$ in $Fe_2O_3$, indicating that there was no $Fe_2O_3$ on a surface of graphene.

The elementary analysis results of the synthesized catalysts are listed in the following Table 2.

TABLE 2

| | Element (At %)[a] | | | | | | | | |
|---|---|---|---|---|---|---|---|---|---|
| Sample | C | O | N | Fe | Au | Pd | Co | Pt | Ag |
| GO | 61.05 | 37.02 | NA | NA | NA | NA | NA | NA | NA |
| N-rGO | 82.06 | 9.85 | 4.18 | NA | NA | NA | NA | NA | NA |
| Pd/N-rGO | 82.07 | 10.05 | 3.85 | NA | NA | 0.32 | NA | NA | NA |

TABLE 2-continued

| Sample | Element (At %)[a] | | | | | | | | |
|---|---|---|---|---|---|---|---|---|---|
| | C | O | N | Fe | Au | Pd | Co | Pt | Ag |
| $Fe_3O_4$/N-rGO | 72.54 | 19.14 | 4.1 | 3.02 | NA | NA | NA | NA | NA |
| Pd/$Fe_3O_4$/N-rGO | 71.54 | 18.88 | 3.95 | 2.95 | NA | 0.31 | NA | NA | NA |
| Ag/$Fe_3O_4$/N-rGO | 71.44 | 19.44 | 4.02 | 2.88 | NA | NA | NA | NA | 0.34 |
| Au/$Fe_3O_4$/N-rGO | 72.03 | 19.78 | 3.81 | 2.84 | 0.22 | NA | NA | NA | NA |
| Pt/$Fe_3O_4$/N-rGO | 71.86 | 18.95 | 3.63 | 2.98 | NA | NA | NA | 0.24 | NA |
| Co/$Fe_3O_4$/N-rGO | 70.86 | 21.05 | 4.11 | 2.78 | NA | NA | 0.29 | NA | NA |
| PdCo/$Fe_3O_4$/N-rGO | 71.25 | 20.01 | 3.93 | 3.01 | NA | 0.32 | 0.30 | NA | NA |
| PdAu/$Fe_3O_4$/N-rGO | 71.56 | 18.76 | 3.87 | 2.92 | 0.23 | 0.33 | NA | NA | NA |
| PdP/$Fe_3O_4$/N-rGO | 72.03 | 19.40 | 3.99 | 2.85 | NA | 0.32 | NA | 0.19 | NA |
| PdAg/$Fe_3O_4$/N-rGO | 72.12 | 18.32 | 3.98 | 2.88 | NA | 0.32 | NA | NA | 0.34 |
| PdCoAu/$Fe_3O_4$/N-rGO | 71.22 | 19.42 | 3.94 | 2.92 | 0.19 | 0.31 | 0.33 | NA | NA |
| PdAg/N-rGO | 83.10 | 9.67 | 4.12 | NA | NA | 0.32 | NA | NA | 0.33 |
| PdAg/$Fe_3O_4$/N-rGO[b] | 73.12 | 17.50 | 3.85 | 2.62 | NA | 0.27 | NA | NA | 0.26 |

[a]An average of values obtained through triplicate XPS analysis, an error <5%, and [b]a catalyst recycled six times As listed in Table 2, it was revealed that the N-doped reduced graphene oxide (N-rGO) included large amounts of oxygen (approximately 10 atomic %) and nitrogen (approximately 4 atomic %). Heteroatoms in the graphene structure can bind to metals, and thus the metal nanoparticles can be polydispersed to prevent re-oxidation of a pure metal $M^0$ (M=Ag, Au, Pt, or Pd).

Figure 5:
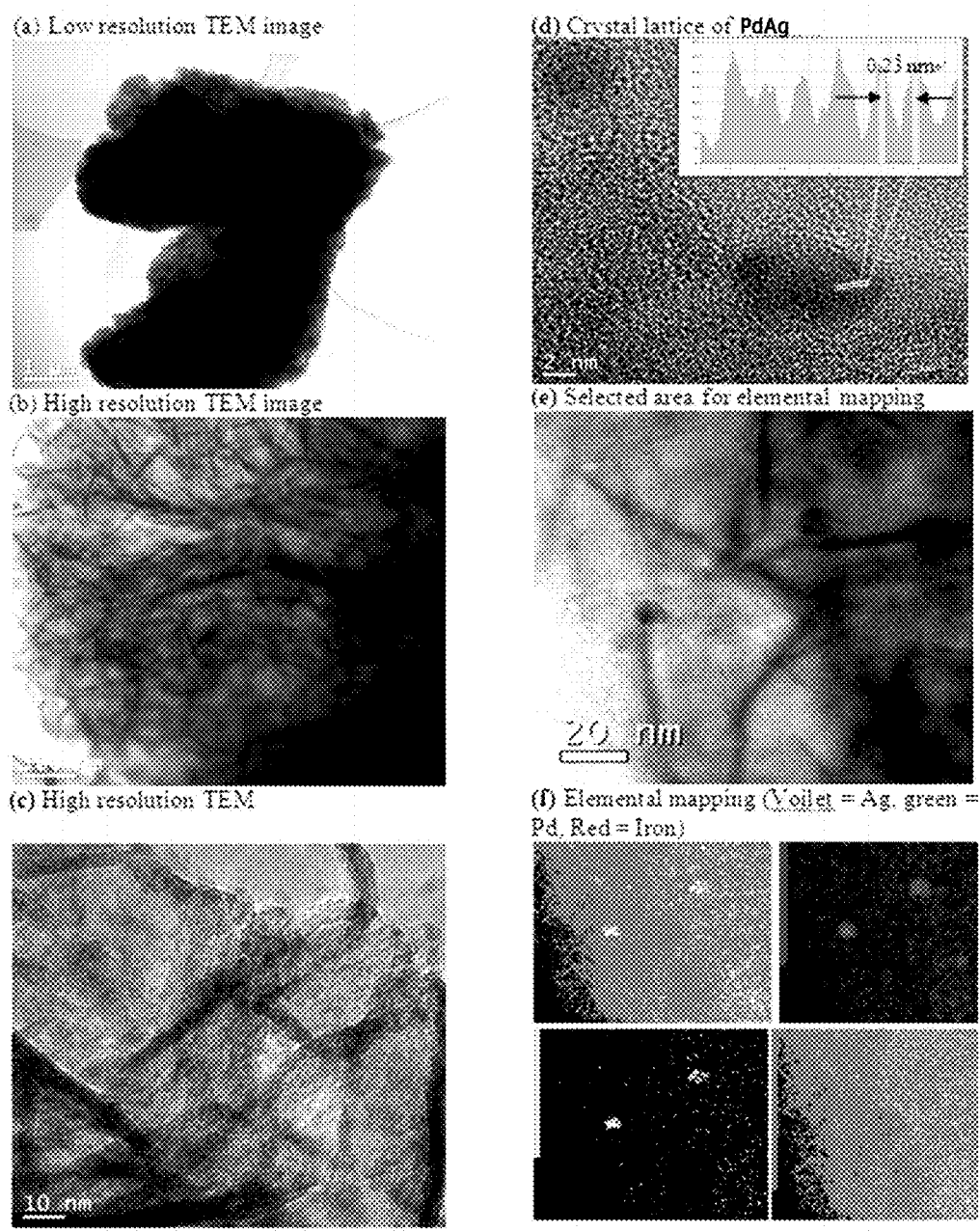
FIG. 5 is a conventional transmission electron microscopy (TEM) image of PdAg/Fe$_3$O$_4$/N-rGO.

Next, a conventional high-resolution TEM (HRTEM) provided with EDX was able to be preferentially used to examine levels of size distribution and condensation of the catalysts (FIG. 5). From these results, it could be seen that the nanoparticles had an average particle size of 5 to 7 nm, and thus were highly monodispersed.

As described above, Fe was uniformly dispersed over N-rGO. From the specific element mapping results of the active catalyst, PdAg/$Fe_3O_4$/N-rGO, according to the present invention, the heterogeneous metal Pd—Ag nanoparticles had a (111) lattice interference distance of 2.3 Å, indicating that the (111) lattice interference distance of 2.3 Å was a value between (111) lattice (0.24 nm) of fcc Ag and (111) lattice (0.22 nm) of fcc Pd. Accordingly, it could be seen that Pd—Ag was formed in the form of an alloy, but did not have a core-shell structure.

Figure 6:
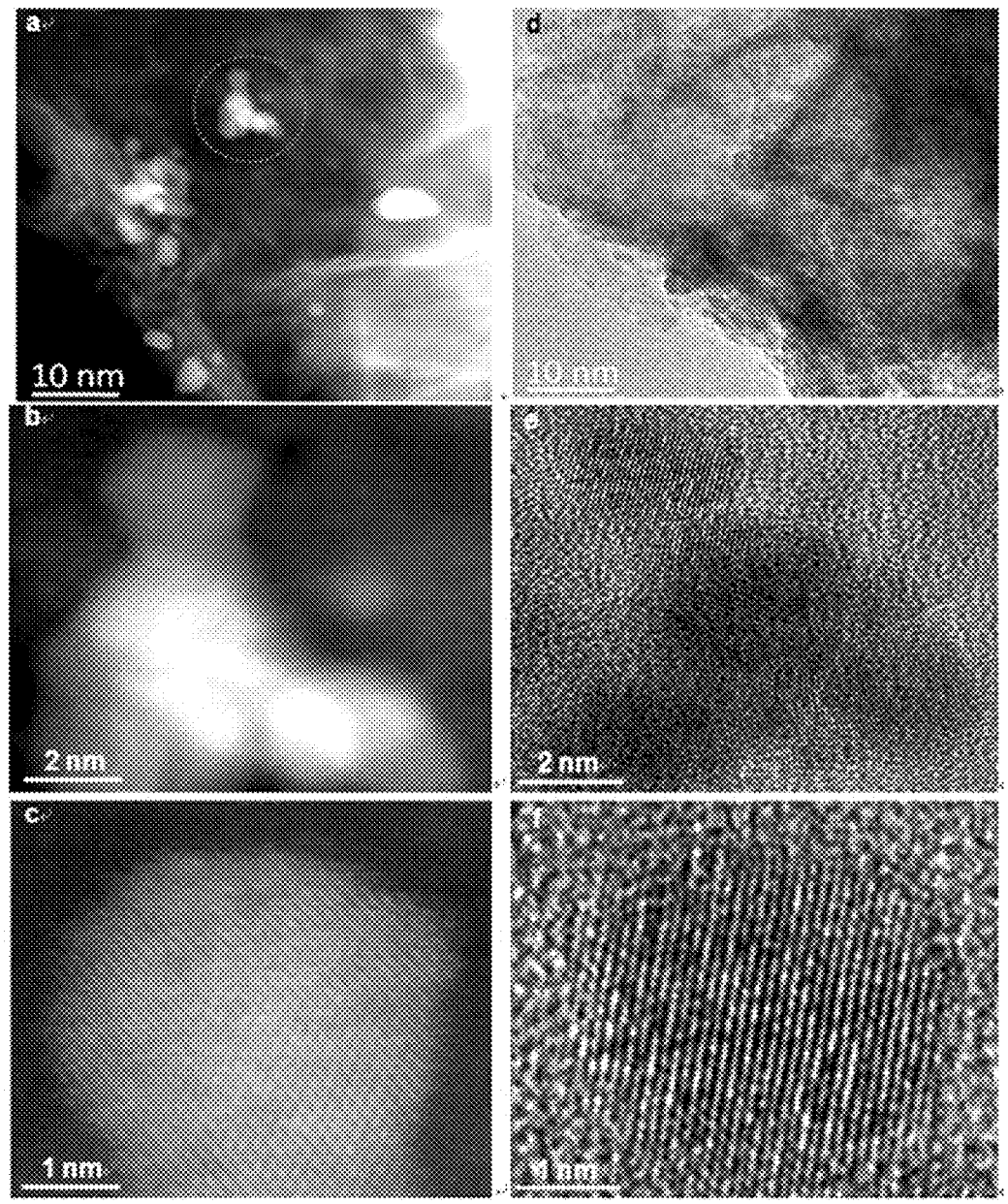
FIG. 6 is a high angle annular dark field (HAADF)-scanning transmission electron microscopy (STEM) image of PdAg/Fe$_3$O$_4$/N-rGO, in which a-c show bright fields at different magnification modes and e-g show dark fields at different magnification modes.

Subsequently, the alloy shape of the PdAg/$Fe_3O_4$/N-rGO catalyst was examined using 200 kV JEOL-2100 HAADF-STEM with probe calibration and a clear resolution of approximately 0.1 nm (FIG. 6). Surprisingly, the STEM results showed that the particle size distribution is wide with a fraction of particles in the range of 3 to 20 nm. Also, the EDX results showed that two metals were located in the same nanoparticles.

Figure 7:
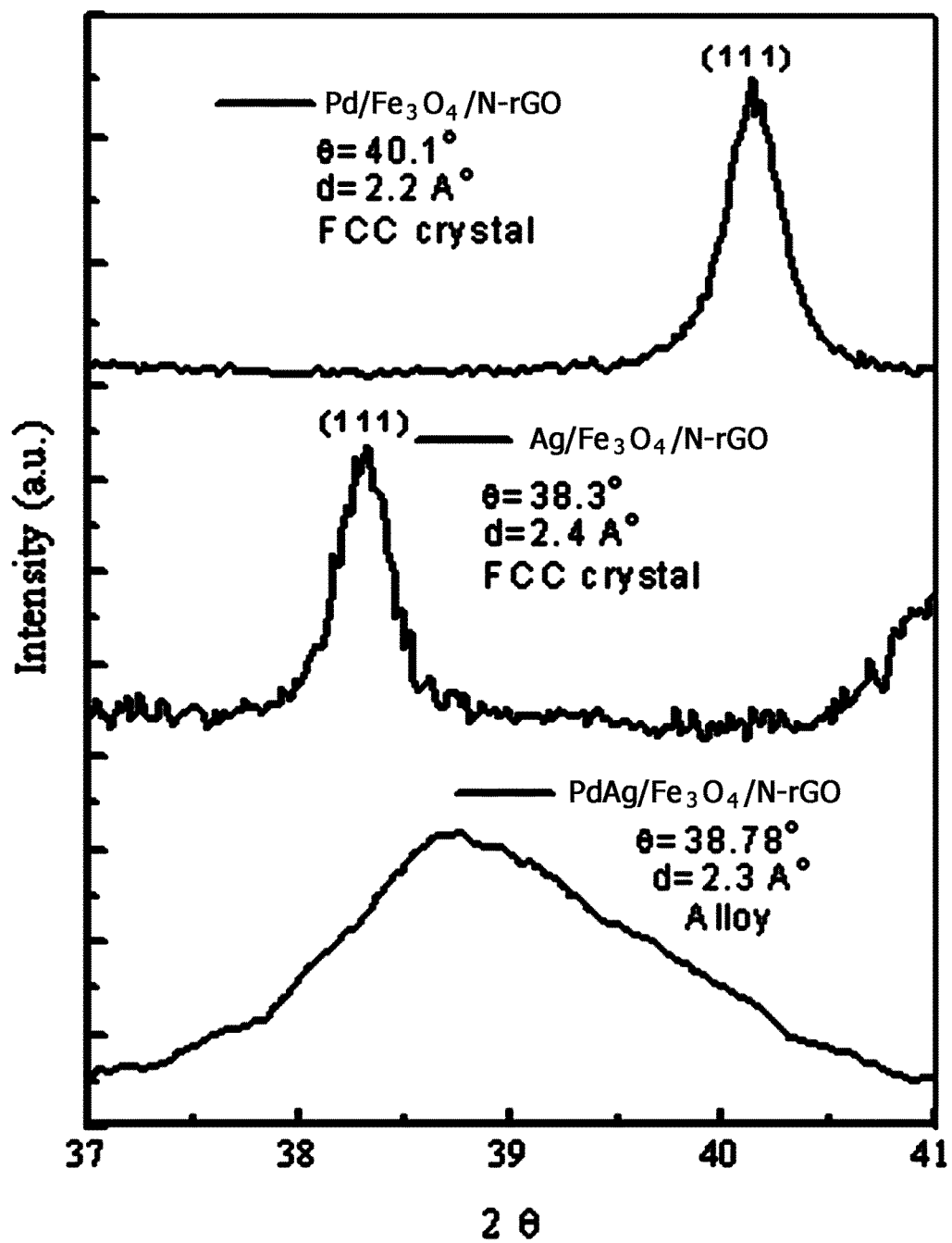
FIG. 7 shows an X-ray diffraction (XRD) pattern in which conversions into Pd/Fe$_3$O$_4$/N-rGO, Ag/Fe$_3$O$_4$/N-rGO, and PdAg/Fe$_3$O$_4$/N-rGO are compared.

Finally, X-ray diffraction (XRD) was used to analyze phase segregation, crystalline behavior, nanoparticle size and changing of lattice parameters (an interspace distance, indices, etc.) of a metal alloy during catalyst preparation or testing under extreme conditions (hydrogenation reaction at a high temperature, etc.). From these results, the XRD pattern of the PdAg/$Fe_3O_4$/N-rGO catalyst was compared with that of the Ag or Pd N-rGO catalyst. The comparison results are shown in FIG. 7. As shown in FIG. 7, it was revealed that the PdAg/$Fe_3O_4$/N-rGO catalyst showed very weak peak intensity at a (111) lattice fringe distance of 2.3 Å. From such a (111) diffraction peak and the Scherrer's formula, the average size of the crystallites was calculated to be 6.2 nm, in good agreement with the value by the conventional HRTEM.

S4. General Procedure for Hydrogenation Reactions of Various Substrates

Next, a general procedure for reduction/hydrogenation was performed: A reactant (0.5 mmol), a catalyst (variable), $H_2O$ (1 mL), formic acid (variable), and an internal standard anisole (1.0 mmol) were filled in a decompression tube (4 mL) sealed with a Teflon lid. The reaction mixture was heated at different temperatures (80° C. and 130° C.) for 10 hours in an oil bath. After completion of reaction, 5 mL of $CH_2Cl_2$ was added thereto. Then, the resulting mixture was centrifuged for 10 minutes to separate a catalyst. The organic layer was analyzed using GC-MS. For these results, see Tables 4 and 5.

S5. Catalytic Reaction Using Hydrogen Gas

A hydrogenation reaction was carried out using a Parr reactor. In a typically process, 76 mg vanillin, 30 mg PdAg/$Fe_3O_4$/N-rGO and 5 mL water were used, the initial pressure of $H_2$ was 1.0 mPa, 150° C., for 1 hour. After the reaction, the Parr reactor was quickly cooled down with a coolant. Thereafter, dichloromethane was added to the reaction mixture to extract an organic compound. The contents of products and substrate were determined by GC-MS.

For these results, see Entry 10 of Table 4.

Experiments S4 and S5 were performed to determine the suitability of the catalysts for practical applications. In these experiments, the efficiency of the PdAg/$Fe_3O_4$/N-rGO catalyst in defunctionalizing carbonyl, alkene, alkyne and nitro groups of many compounds was determined. This method was considered to be most effective for upgraded bio-fuels, and the most challenging reaction was accompanied with direct hydrodeoxygenation of carbon-oxygen bonds in an aromatic aldehyde. Frequently occurring direct hydrodeoxygenation leads to significant amounts of undesired products (aromatic alcohols, methylcyclohexane and benzenes). Also, a general approach is to reduce aldehydes/ketones into alkanes in the presence of aniline.

Direct hydrodeoxygenation of aromatic aldehydes and ketones with hydrogen produced in situ from formic acid was attempted with the catalyst to produce a variety of industrially applicable synthetic feedstocks, and the results obtained from such experiments are listed in the following Table 3. The results of Table 3 showed that aldehydes containing various functionalities were very easily converted into aromatic compounds selectively substituted with a methyl group at 130° C. Although not listed in Table 3, the selectivity was better than 99% for all the molecules tested whenever the conversion occurred in all the experiments.

Meanwhile, possible reaction pathways for dual role played by PdAg/$Fe_3O_4$/N-rGO catalyst may start with dissociative adsorption of formic acid on Pd, as postulated earlier for the Pd complex catalyst), which leads to formation of metal hydride complex upon releasing carbon dioxide. Then, the metal hydride complex selectively converts C—O, C—C and N—O multiple bonds into reduced compounds.

Meanwhile, one reaction was carried out in the same manner as described above in Experiment S5 using the PdAg/Fe$_3$O$_4$/N-rGO catalyst according to the present invention and hydrogen gas supplied from the outside without using formic acid (a H$_2$ source) (See Entry 10 of Table 3). As a result, it was confirmed that the aromatic aldehydes were completely reduced. From these results, it was expected that the catalyst according to the present invention plays the dual role of dehydrogenating formic acid and hydrogenating organic compounds. In the Ag—Pd alloy catalyst, Ag can serve as a promoter.

Also, it was confirmed that the aromatic ketone, for example, acetophenone, benzophenone and fluorenone, were also selectively hydrodeoxygenated into aromatic alkanes (see Entries 11 to 13 of Table 3). Further, it was revealed that any substrates containing an amide and an ester substituted were selectively converted into the corresponding soft alkanes (see Entries 14 and 15 of Table 3).

Further, the novel PdAg/Fe$_3$O$_4$/N-rGO catalyst according to the present invention was only sensitivite to aromatic carbonyl groups, but exhibited no activities to the aliphatic carbonyl groups (see Entries 16 and 20 of Table 3). This difference could be explained by considering the bond interaction between catalyst and graphene support. In this case, the aromatic carbonyl group provides an activated site for a hydrodeoxygenation reaction, but the aliphatic carbonyl group could not interact with the graphene support. From these facts, it could be seen that selective hydrogenation caused by hydrodeoxygenation of the catalyst occurred.

TABLE 3

| Entry | Substrate | Temp (° C.) | Conversion (%)$^a$ |
|---|---|---|---|
| 1 | 4-hydroxy-3-methoxybenzaldehyde (HO—, H$_3$CO— on benzene, —CHO) | 80 / 130 | 5 / 99 |
| 2 | 4-hydroxy-3-ethoxybenzaldehyde (HO—, H$_3$CH$_2$CO—, —CHO) | 80 / 130 | 22 / 99 |
| 3 | 4-hydroxy-3-methylbenzaldehyde (HO—, H$_3$C—, —CHO) | 80 / 130 | 24 / 99 |
| 4 | 3,4-dimethylbenzaldehyde (H$_3$C—, H$_3$C—, —CHO) | 80 / 130 | 43 / 99 |
| 5 | 2-hydroxy-3-methoxybenzaldehyde (H$_3$CO—, OH, —CHO) | 80 / 130 | 2 / 90 |
| 6 | 2-hydroxybenzaldehyde (OH, —CHO) | 80 / 130 | 0 / 70 |
| 7 | 4-methoxybenzaldehyde (H$_3$CO—, —CHO) | 80 / 130 | 4 / 90 |
| 8 | benzaldehyde (—CHO) | 80 / 130 | 0 / 30 |
| 9 | pyridine-4-carbaldehyde (N-pyridyl —CHO) | 80 / 130 | 0 / 20 |
| 10$^b$ | 4-hydroxy-3-methoxybenzaldehyde (HO—, H$_3$CO—, —CHO) | 150 | 99 |
| 11 | acetophenone (Ph—C(O)—CH$_3$) | 80 / 130 | 3 / 90 |
| 12 | benzophenone (Ph—C(O)—Ph) | 80 / 130 | 46 / 99 |
| 13 | fluorenone | 80 / 130 | 52 / 99 |
| 14 | isatin (1H-indole-2,3-dione) | 80 / 130 | 1 / 80 |
| 15$^b$ | ethyl 3-oxo-3-phenylpropanoate (Ph—C(O)—CH$_2$—C(O)—O—Et) | 80 / 130 | 12 / 99 |
| 16$^b$ | 1-methylindolin-2-one | 80 / 130 | 0 / 0 |
| 17$^b$ | menthone (2-isopropyl-5-methylcyclohexan-1-one) | 80 / 130 | 0 / 0 |

TABLE 3-continued

| Entry | Substrate | Temp (°C.) | Conversion (%)[a] |
|---|---|---|---|
| 18[b] | (phenylacetaldehyde: PhCH2CH2CHO) | 80<br>130 | 0<br>0 |
| 19[b] | (phenylacetone: PhCH2C(O)CH3) | 80<br>130 | 0<br>0 |
| 20 | (cyclohexanone) | 80<br>130 | 0<br>0 |

[a]Reaction conditions: a substrate (0.5 mmol), formic acid (2.5 equivalents), a catalyst (30 mg), water (1 mL), and a specific reaction time of 6 hours: In all cases, observed with selectivity of >99%,
[a]the conversion rate and selectivity analyzed through GC (anisole used as the internal standard),
[b]Performed with hydrogen gas (5 mL of water, a H2 pressure of 1.0 MPa, a reaction time of 1 hour, a catalytic amount of 30 mg, and a reaction temperature of 150° C.), wherein the conversion rate and selectivity are represented by an average of values obtained from experiments conducted in triplicate.

Meanwhile, From a synthetic point of view, selective hydrogenation of alkene, alkyne, and nitroarene provides valuable building blocks for the preparation of a variety of agrochemicals, upgraded biodiesels, and pharmaceuticals.

Accordingly, hydrogenation of the substrates including cyclic and acyclic olefins, unsaturated aldehydes, unsaturated ketones and other unsaturated carbonyl compounds was examined (see Entries 1 to 7 of Table 4). The presence of substituted functional groups such as aldehydes, acids and alcohols had no influence on hydrogenation of the alkenes, and thus an excellent conversion rate and selectivity were generally achieved.

In some cases as in phenylacetylene and nitrobenzene, a higher equivalent amount of formic acid (3.5) was required for significant conversion (see Entries 8 and 9 of Table 4). For selective hydrogenation of nitroarenes into anilines, it was desirably observed that nitrobenzene was completely converted into aniline with 99% selectivity at 80° C. using hydrogen produced in situ from formic acid under atmospheric pressure (see Entry 9 of Table 4).

Also, when the heterogeneous metal catalyst was an aromatic amine, the metal catalyst was able to be used to synthesize a methyl-substituted amide in a single procedure instead of a conventional two-step procedure (including a first step of aniline methylation and a second step of formylation). It was confirmed that aniline was synthesized into N-methyl N-phenol formamide in a single step according to a representative reaction (see Entry 10 of Table 4).

TABLE 4

| Entry | Substrate | Product | Temperature (°C.) | Conversion (%)[g] | Selectivity (%)[g] |
|---|---|---|---|---|---|
| 1[a] | (1-decene) | (decane) | 80 | 99 | 99 |
| 2[a] | (HO-terminated alkene) | (HO-terminated alkane) | 80 | 99 | 99 |
| 3[a] | (terminal alkene) | (alkane) | 80<br>130 | 91<br>99 | 99<br>99 |
| 4[a] | (cyclohex-2-enone) | (cyclohexanone) | 80<br>130 | 90<br>99 | 99<br>99 |
| 5[a] | (cinnamaldehyde) | (PhCH2CH2CHO) | 80 | 99 | 99 |
| 6[a] | (cinnamic acid) | (PhCH2CH2COOH) | 80 | 99 | 99 |
| 7[a] | (flavone) | (flavanone) | 80<br>130 | 5<br>60 | 48<br>47 |
| 8[b] | (phenylacetylene) | (ethylbenzene) | 130 | 80 | 90 |
| 9[c] | (nitrobenzene) | (aniline) | 80 | 99 | 99 |

TABLE 4-continued

| Entry | Substrate | Product | Temperature (°C.) | Conversion (%)[g] | Selectivity (%)[g] |
|---|---|---|---|---|---|
| 10[d] | ⟨benzene⟩—NH$_2$ | ⟨benzene⟩—NCHO | 140 | 80 | 75 |

(Note)
Reaction conditions: a substrate (0.5 mmol), water (1 mL),
[a] formic acid (1.5 equivalents), a catalyst (30 mg), a specific reaction time of 6 hours,
[b] formic acid (3.5 equivalents), a catalyst (30 mg), a specific reaction time of 12 h hours,
[c] formic acid (3.5 equivalents), a catalyst (30 mg), a specific reaction time of 6 hours,
[d] formic acid (3.0 equivalents), a catalyst (50 mg), a specific reaction time of a 24 hours,
[g] the conversion rate and selectivity analyzed through GC (anisole used as the internal standard), wherein the conversion rate and selectivity are represented by an average of values obtained from experiments conducted in triplicate. A 1% experimental error represents high reproducibility of the data.

S6. Recycling of Catalyst

After each of the reactions according to Experiments S3 and S4 as described above, the PdAg/Fe$_3$O$_4$/N-rGO catalyst was centrifuged and magnetically separated, washed three times with water and then with acetone, and dried at 120° C. for 2 hours in an oven. Thereafter, the recovery rate was checked using the same catalyst as a reagent, and the catalytic effect was calculated from the reactions repeatedly conducted six times. The results are summarized and listed in the following Table 5, and the elementary analysis results are listed in Table 2.

TABLE 5 vanillin —a→ 2-methoxy-4-methylphenol

| Entry | Recycle | Conversion (%)[b] | Selectivity (%)[b] |
|---|---|---|---|
| 1 | Fresh | 99 | >99 |
| 2 | 1st | 99 | >99 |
| 3 | 2nd | 99 | >99 |
| 4 | 3rd | 99 | >99 |
| 5 | 4th | 98 | >99 |
| 6 | 5th | 98 | >99 |
| 7 | 6th | 97 | >99 |

(Note)
Reaction conditions:
(a) vanillin (0.5 mmol), S/C = 333, formic acid (2.5 equivalents), water (1 mL), a specific reaction time of 2 hours, a temperature of 130° C.;
[b] the conversion rate based on GC analysis (anisole used as the internal standard) and calculated as an average of values measured in duplicate, and a data error of <2%.

The high stability, easy separability and recoverability without loss of activities of the catalyst were important for actual applications. In a model reaction using vanillin, it could be seen that the loss of the activities of the catalyst was negligibly low even when the catalyst was recycled six times, as listed in Table 5.

The selectivity of all the catalysts to 2-methoxy-4-methylphenol was constantly maintained even when recycled six times. In addition, it was confirmed that the catalysts were able to be easily separated from a reaction solution using a method such as magnetism or filtration/centrifugation.

Figure 8:
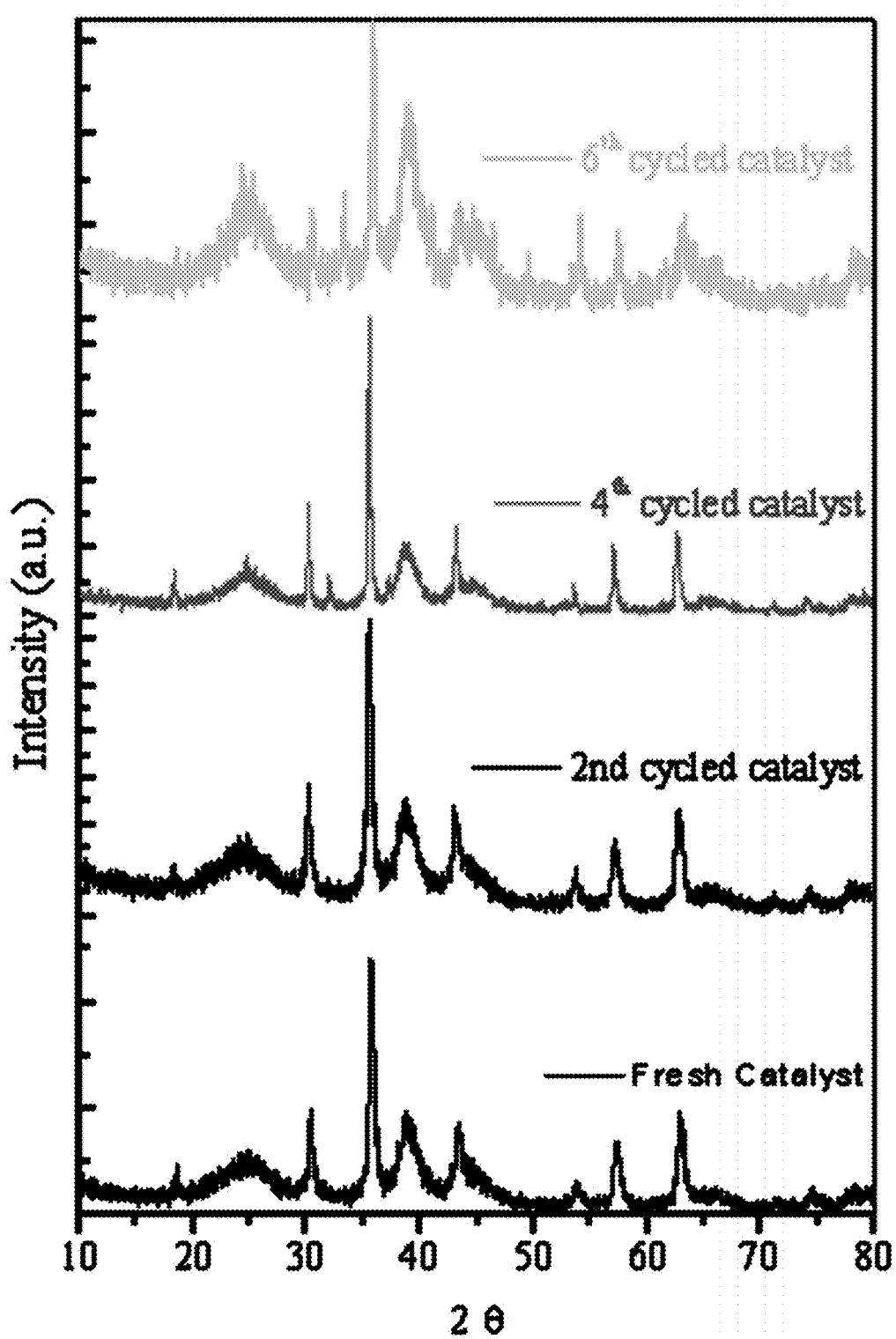
FIG. 8 is an XRD pattern of a PdAg/Fe$_3$O$_4$/N-rGO catalyst in a recycling test.
Figure 9:
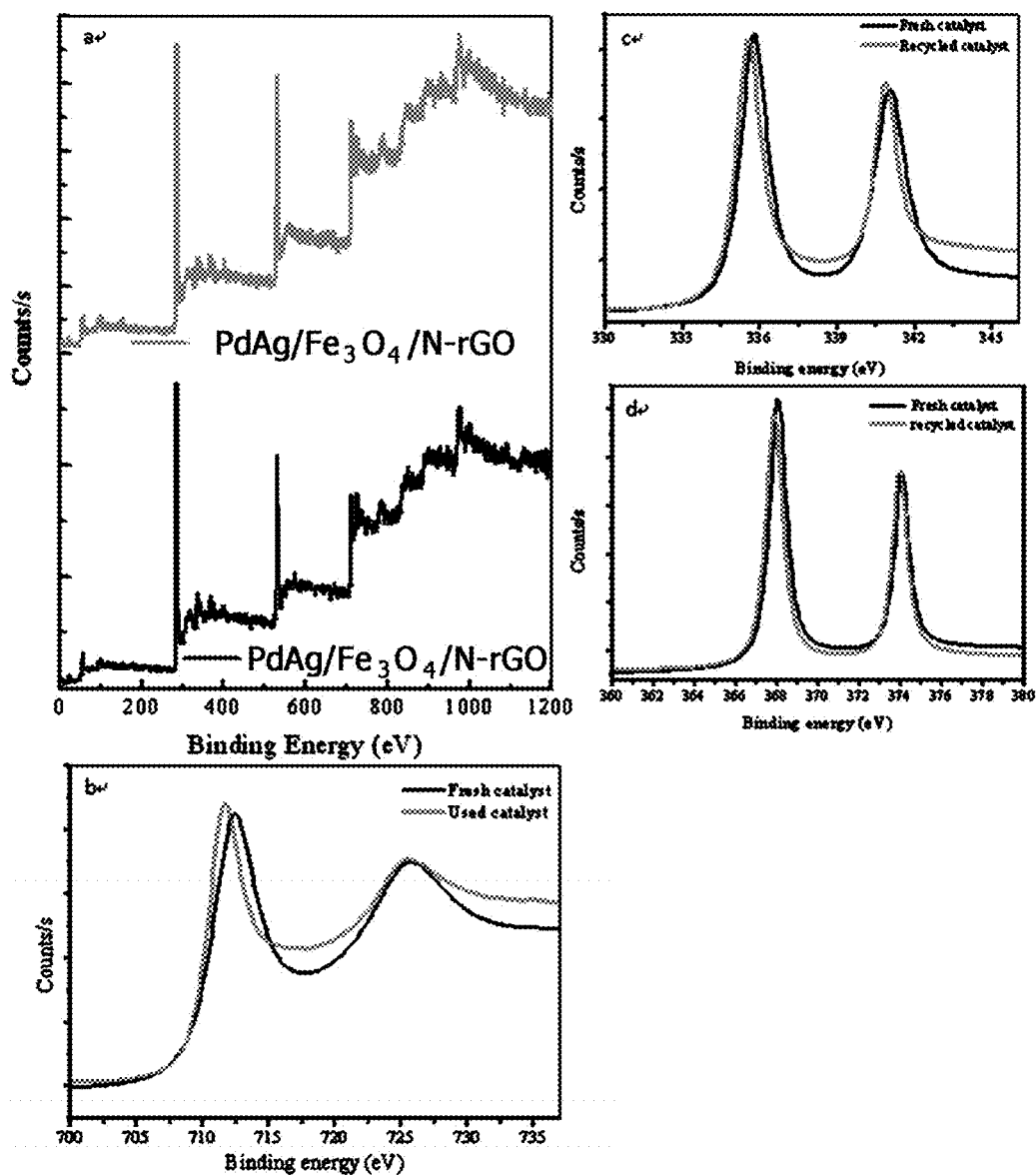
FIG. 9 is a diagram showing the XPS analyses of surfaces of a fresh PdAg/Fe$_3$O$_4$/N-rGO catalyst (a fresh catalyst or a fresh PdAg/Fe$_3$O$_4$/N-rGO) and a PdAg/Fe$_3$O$_4$/N-rGO catalyst recycled six times (a recycled catalyst or PdAg/Fe$_3$O$_4$/N-rGO re-used six times), in which (a) shows an XPS full scan, (b) shows Fe2p spectra, (c) shows Pd3d spectra, and (d) shows Ag3d spectra.

After each periodic reaction, the catalysts in the form of a complex were checked through XRD, and the slightly increased peak intensity of Pd—Ag was observed after the 4th recycling, indicating that the catalysts started to condense, but such condensation did not have an influence on catalytic activities (FIG. 8). To check possible leaching of the metal catalysts during a reaction, the mixture was analyzed using inductive coupled plasma emission spectroscopy (ICP-ES). As a result, it was revealed that the metal catalysts were leached at an amount of less than 0.1 ppm, indicating that negligible levels of Ag and Pd were leached into the reaction mixture. These facts showed that the heteroatoms (N and O) of N-rGO were bound to reactive atoms in the metal catalysts at a low content of less than 0.6 atomic %, which clearly indicated that the heteroatoms were uniformly dispersed on surfaces of the metal catalysts. The surfaces of the catalysts recycled six times were analyzed in detail through XPS. As a result, it was revealed that there was little change in atomic contents of elements present on the surface of the catalyst (see Table 2 and FIG. 9).

The present invention provides a catalyst that is stable and exhibits a high conversion rate and high selectivity for hydrogenation by removing functional groups from a biomass, preferably an aromatic compound containing a carbonyl group derived from the biomass. Such a catalyst has advantages in that the catalyst can be easily separated after a hydrogenation reaction, and the catalytic activities are not significantly altered even when the catalyst is recovered and repeatedly recycled.

Also, the present invention provides a hydrogenation method in which, when such a catalyst is used, hydrogen can be directly produced in a reactor using formic acid as a hydrogen source without supplying additional hydrogen gas and can be used at the same time. The hydrogenation method has economic advantages in that the method can be carried out under mild reaction conditions, and thus can minimize reaction procedures, reduce the risks caused by the supply of additional hydrogen gas, and separate and recycle the catalyst from reaction products after a reaction.

Further, high-value-added hydrocarbon compounds can be easily prepared from inexpensive biomasses at high yield, which results in contribution to cost saving and industry development.

It will be apparent to those skilled in the art that various modifications can be made to the above-described exemplary embodiments of the present invention without departing from the scope of the invention. Thus, it is intended that the present invention covers all such modifications provided they come within the scope of the appended claims and their equivalents.

What is claimed is:

1. A hydrogenation catalyst, comprising:
   inorganic nanoparticles; and
   a nitrogen-doped reduced graphene oxide support for supporting the inorganic nanoparticles;
   wherein the inorganic nanoparticles comprise silver nanoparticles, palladium nanoparticles, and $Fe_3O_4$ nanoparticles.

2. The hydrogenation catalyst of claim 1, wherein the inorganic nanoparticles have an average particle size of 3 to 10 nm.

3. The hydrogenation catalyst of claim 1, wherein the hydrogenation catalyst comprises the inorganic nanoparticle at 1 to 5 atomic %.

4. A method of manufacturing a hydrogenation catalyst, comprising:
   obtaining a nitrogen-doped reduced graphene oxide by reacting a nitrogen-containing compound with a colloidal suspension of graphene oxide;
   obtaining a dispersion of the nitrogen-doped reduced graphene oxide by dispersing the nitrogen-doped reduced graphene oxide in water;
   dispersing the dispersion of the nitrogen-doped reduced graphene oxide by adding an aqueous solution of an inorganic nanoparticle precursor to the dispersion of the nitrogen-doped reduced graphene oxide, wherein the inorganic nanoparticle precursor comprises salts of silver, palladium and iron; and
   adding a reducing agent to perform a reaction.

5. The method of claim 4, wherein the inorganic nanoparticle precursor is selected from the group consisting of a chloride, a sulfate, a nitrate, a carbonate of the inorganic nanoparticle, and a mixture thereof.

6. The method of claim 4, wherein the reducing agent is selected from the group consisting of hydrazine, hydrazine hydrate, a borohydride, sodium borohydride, and a mixture thereof.

7. A method of hydrogenating a biomass-derived hydrocarbon compound, comprising:
   a hydrogenation operation of allowing a hydrocarbon compound as a substrate to react with the catalyst of claim 1 in the presence of a hydrogen source,
   wherein the hydrocarbon compound is derived from a biomass and contains a functional group.

8. The method of claim 7, wherein the hydrogen source is formic acid.

9. The method of claim 7, wherein the hydrogenation operation is performed without supplying hydrogen gas from the outside of a reactor.

10. The method of claim 7, wherein the hydrogenation operation is performed under reaction conditions of 80 to 130° C. and 6 to 12 hours.

11. The method of claim 7, wherein the hydrogen source is used at an equivalent content of 1.5 to 3.5 moles, based on the total content of the substrate.

12. The method of claim 7, wherein the hydrocarbon catalyst is used at a content of 1.8 to 4.0 g per mole of a reaction product, based on the total content of the inorganic nanoparticles included in the catalyst.

13. The method of claim 7, wherein the substrate is at least one compound selected from the group consisting of an aromatic compound containing a carbonyl group, a hydrocarbon compound containing an alkene group, a hydrocarbon compound containing an alkyne group, and a hydrocarbon compound containing a nitro group.

14. The method of claim 13, wherein the substrate is vanillin.

15. The method of claim 7, wherein the catalyst comprises the inorganic nanoparticles having an average particle size of 3 to 10 nm.

16. The method of claim 7, wherein the catalyst comprises the inorganic nanoparticle at a content of 1 to 5 atomic %.

17. The method of claim 7, further comprising:
   recovering the catalyst after the hydrogenation operation.

18. The method of claim 17, wherein the recovering of the catalyst is performed using at least one method selected from the group consisting of centrifugation, filtration, and a magnetic method.

* * * * *